United States Patent [19]

Fox, Jr.

[11] 4,078,058

[45] Mar. 7, 1978

[54] CERIUM SULFADIAZINE FOR TREATING BURNS

[75] Inventor: Charles L. Fox, Jr., Sherman, Conn.

[73] Assignee: Research Corporation, New York, N.Y.

[21] Appl. No.: 704,817

[22] Filed: Jul. 13, 1976

[51] Int. Cl.$^2$ .................... A61K 31/63; C07D 239/44
[52] U.S. Cl. ................ 424/228; 260/239.75; 424/DIG. 13
[58] Field of Search .................. 424/228, 287; 260/239.75

[56] References Cited

U.S. PATENT DOCUMENTS

| | | | |
|---|---|---|---|
| 2,410,793 | 11/1946 | Winnek et al. | 260/239.75 |
| 3,761,590 | 9/1973 | Fox, Jr. | 424/228 |

OTHER PUBLICATIONS

*Chemical Abstracts*, vol. 48 3918–3919.

*Primary Examiner*—Frederick E. Waddell
*Attorney, Agent, or Firm*—Cooper, Dunham, Clark, Griffin & Moran

[57] ABSTRACT

Cerium sulfadiazine and compositions containing a cerium sulfadiazine, particularly cerous sulfadiazine [Ce(SD)$_3$] wherein SD represents the sulfadiazine moiety, have been found to be useful in the treatment of burns. Cerous sulfadiazine is prepared by reacting an aqueous solution of sodium sulfadiazine with an aqueous solution of a cerous salt, such as cerous nitrate or cerous chloride. The resulting cerous sulfadiazine is formed as a white precipitate. The precipitated cerous sulfadiazine, such as made by reacting cerous nitrate with sodium sulfadiazine, upon washing and drying has a melting point of 248°–255° C.

19 Claims, 4 Drawing Figures

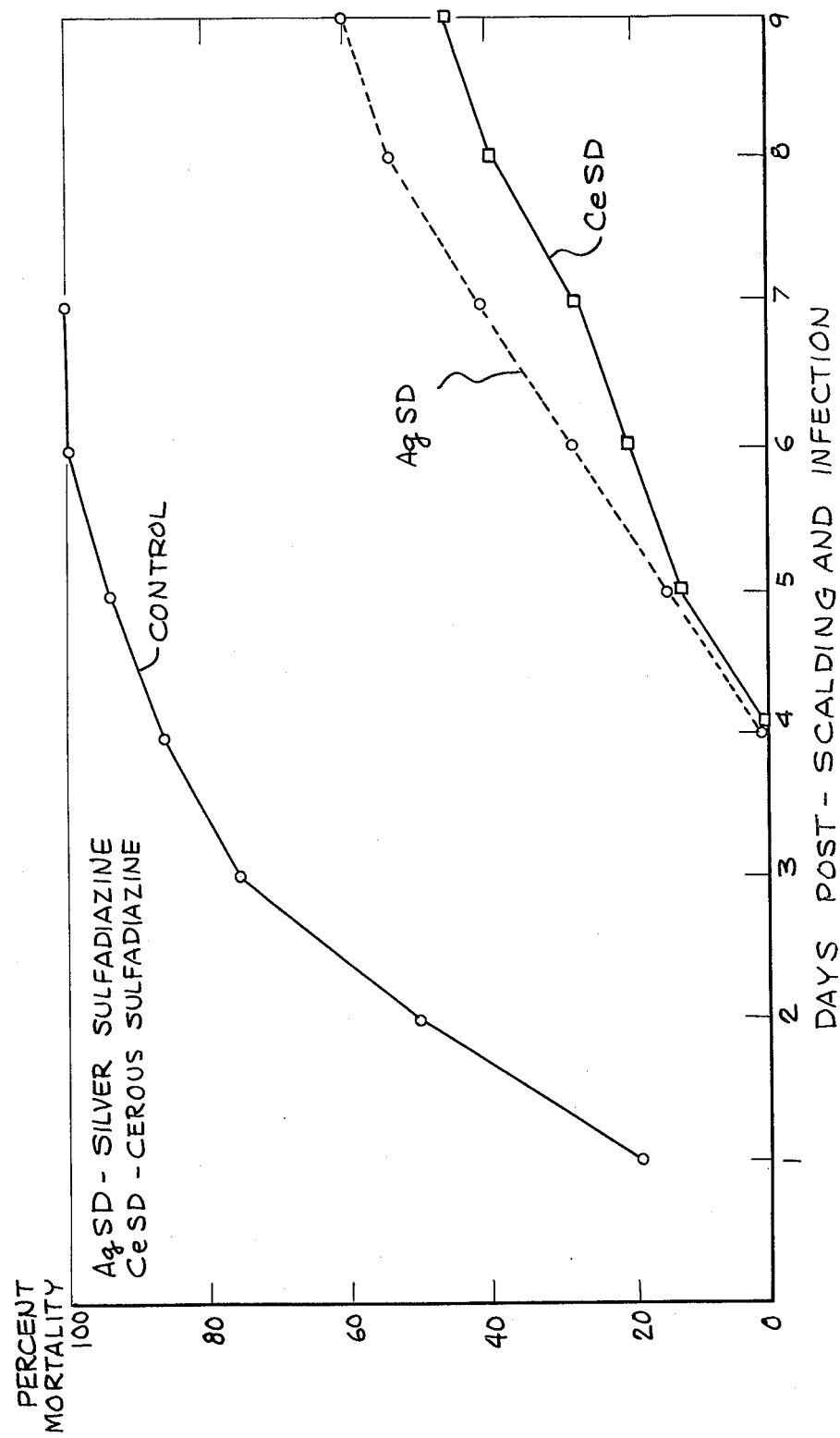

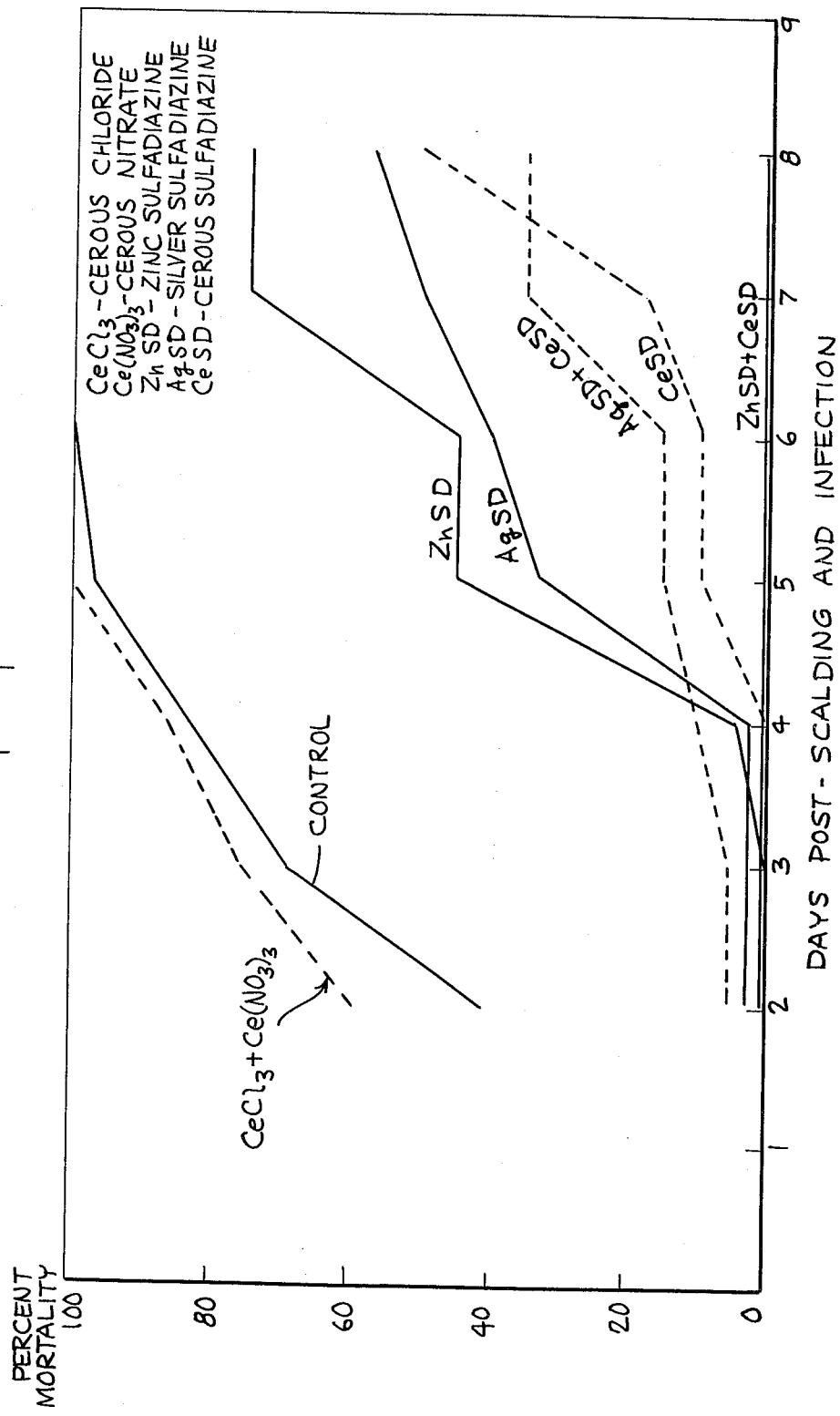

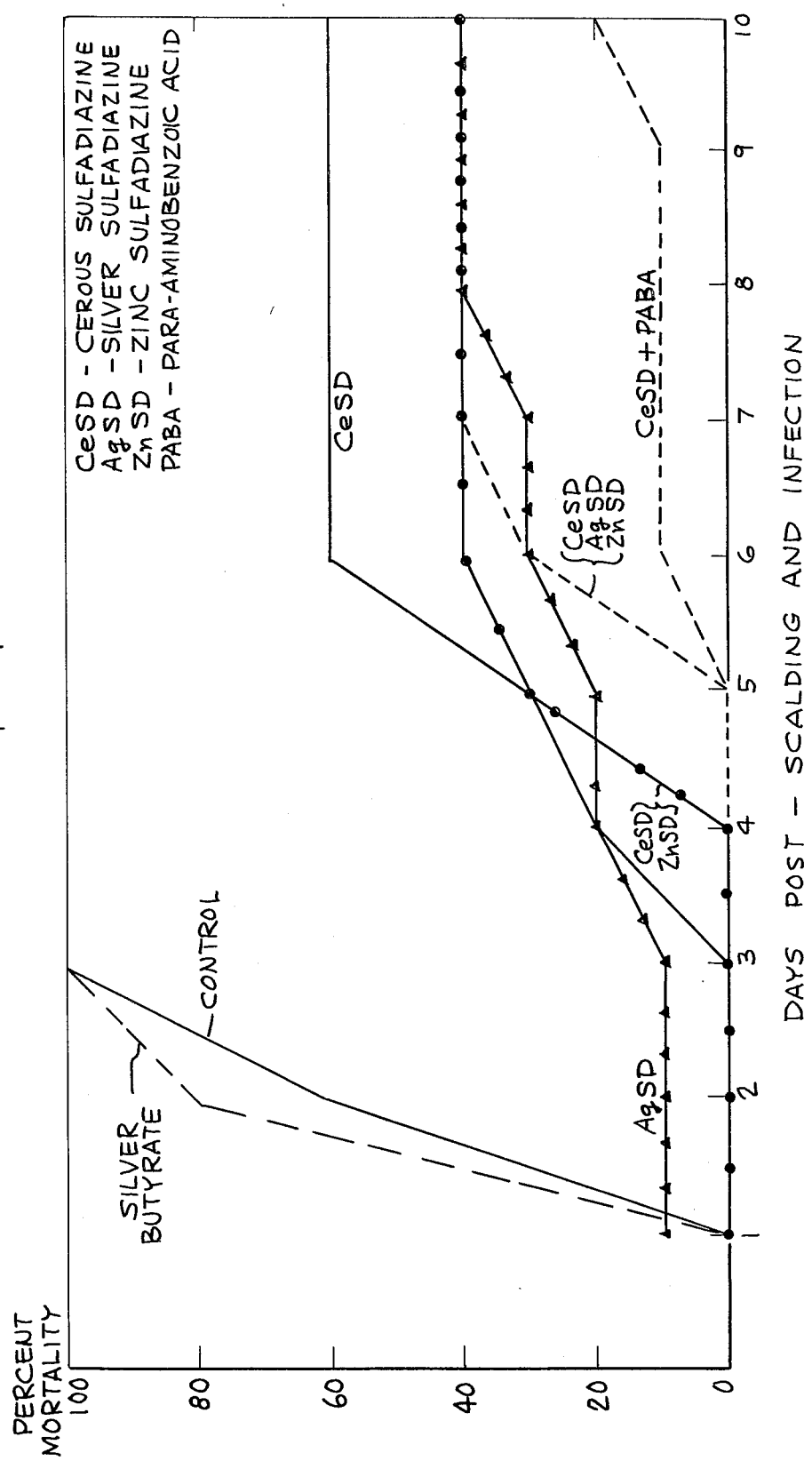
Fig. III.

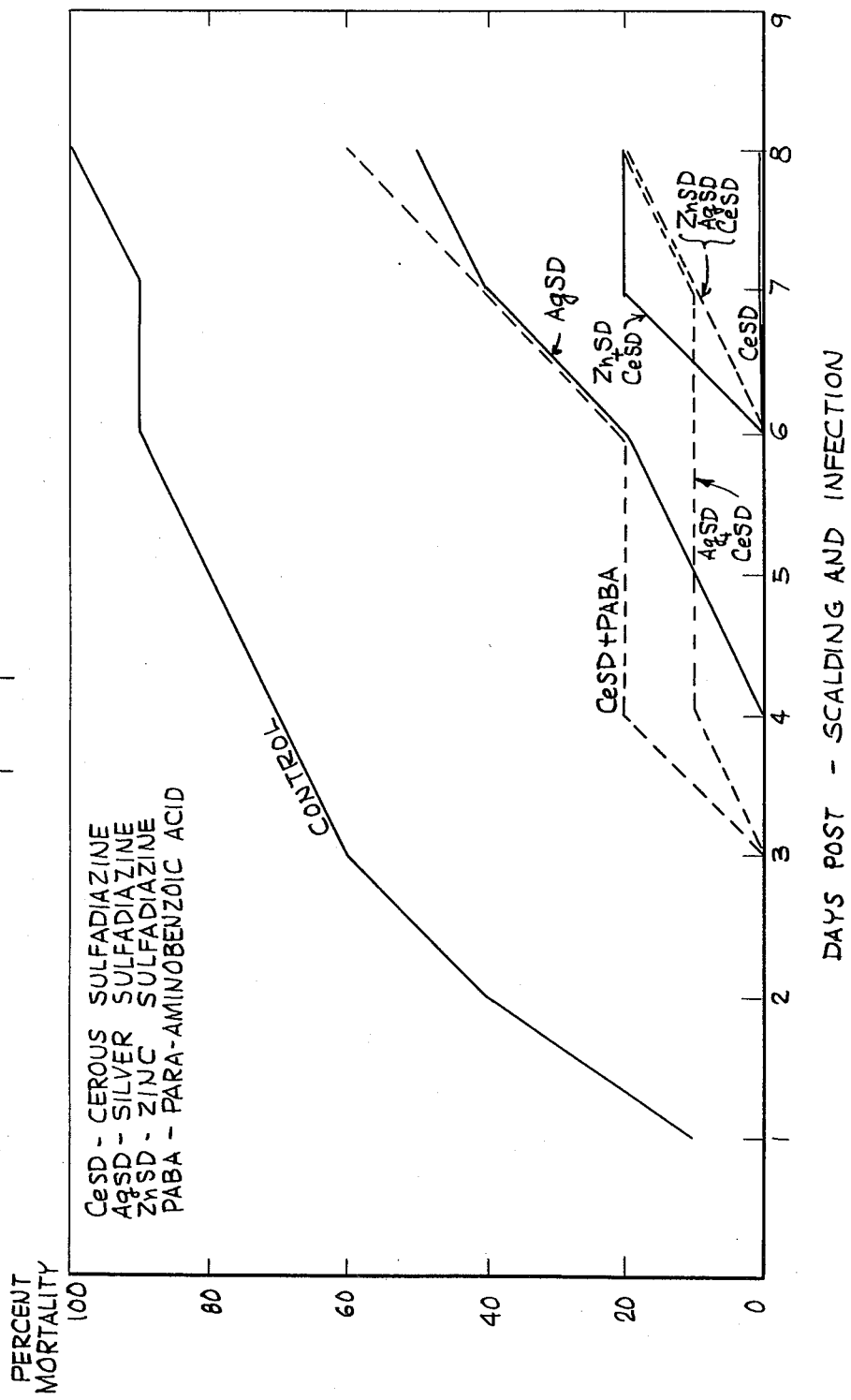

CERIUM SULFADIAZINE FOR TREATING BURNS

This invention relates to compounds and compositions, methods of making the same and methods of employing the same for the treatment of burns.

In U.S. Pat. Nos. 3,761,590 and 3,792,161 silver sulfadiazine is disclosed as being useful in the treatment of burns. In copending, coassigned patent application Ser. No. 560,103 filed Mar. 19, 1975 zinc sulfadiazine is disclosed as being useful in the treatment of burns. Further, in copending, coassigned patent application Ser. No. 663,052 filed Mar. 2, 1976 water-soluble cerium salts, such as cerous nitrate, particularly in combination with silver sulfadiazine, are disclosed as being useful in the treatment of burns. The disclosures of the above-identified U.S. patents and patent applications are herein incorporated and made part of this disclosure.

It is an object of this invention to provide compounds and compositions containing said compounds useful in the treatment of burns.

It is another object of this invention to provide a method of preparing compounds and compositions containing said compounds and techniques employing the same for the treatment of burns.

In at least one embodiment of the practices of this invention at least one of the foregoing objects will be achieved.

How these and other objects of this invention are achieved will become apparent in the light of the accompanying disclosure and drawings wherein:

FIGS. I through IV graphically illustrate the results achievable in accordance with the practices of this invention for the treatment of burns.

It has been discovered that a cerium sulfadiazine or cerium salt or derivative of sulfadiazine, especially cerous sulfadiazine, is useful in the treatment of burns. Cerous sulfadiazine is prepared by reacting a water-soluble cerous salt with sulfadiazine, such as by reacting an aqueous solution of cerous nitrate or cerous chloride with an aqueous solution of sodium sulfadiazine. When these aqueous solutions are reacted, such as by merely admixing the solutions, poorly water-soluble cerous sulfadiazine (solubility about 550 mg/100 ml, approximately 0.5% by wt.) is precipitated.

Cerous sulfadiazine is preferred in the practices of this invention in the treatment of burns, particularly cerous sulfadiazine prepared by reacting an aqueous solution of a water-soluble cerous salt, such as cerous nitrate or cerous chloride, with an aqueous solution containing sulfadiazine, such as an aqueous solution of sodium sulfadiazine. When an aqueous solution of cerous nitrate is admixed with an aqueous solution of sodium sulfadiazine, cerous sulfadiazine is precipitated. The precipitated cerous sulfadiazine, $[Ce(SD)_3]$ wherein SD represents the sulfadiazine moiety, upon washing and drying has a melting point of 248°–255° C. Cerous sulfadiazine is also prepared, as would be apparent from the above, by reacting an aqueous solution of sodium sulfadiazine and an aqueous solution of cerous chloride.

In the preparation of cerium sulfadiazine, particularly cerous sulfadiazine, in accordance with this invention it is preferred to employ water-soluble cerium salts of inorganic acids for reacting an aqueous solution thereof with an aqueous solution containing sulfadiazine, such as an alkali metal sulfadiazine, e.g. sodium sulfadiazine. Suitable cerium salts for the preparation of cerium sulfadiazine in accordance with this invention include the water-soluble cerium salts, cerous nitrate, cerous acetate and its hydrate, cerous chloride, basic cerium nitrate $Ce(OH)(NO_3)_3.3H_2O$, cerous sulfate, cerous bromite $Ce(BrO_3)_3.9H_2O$, cerous bromide $CeBr_3.H_2O$, the cerium iodates $Ce(IO_3).H_2O$ and $Ce(IO_3)_4$, cerous iodide $CeI_3.9H_2O$, cerous chloride $CeCl_3$, cerous nitrate $Ce(NO_3)_3.6H_2O$, cerium sulfate $Ce(SO_4)_2$ which forms basic salts and cerous oxalate $Ce(C_2O_4)_3.9H_2O$. In accordance with one practice of this invention cerium sulfadiazine, such as cerous sulfadiazine, is prepared by reacting an alkaline aqueous solution of sulfadiazine (such as is prepared by adding sodium hydroxide and sulfadiazine to water) with an aqueous solution of a water-soluble cerous salt, such as cerous acetate.

Demonstrative of the antibacterial properties of cerous sulfadiazine prepared in accordance with this invention, cerous sulfadiazine was tested along with inorganic cerium salts, silver sulfadiazine, zinc sulfadiazine and sodium sulfadiazine in a nutrient broth. In these tests bacterial growth was measured or observed by turbidity in the test tubes containing the inoculated nutrient broth after 18–20 hours incubation at 37° C. The inorganic salts of cerium, e.g. cerous nitrate, were inhibitory only at a relatively high concentration of at least 1.0 $\mu$M per ml or higher. In marked contrast, cerous sulfadiazine inhibited bacterial growth at a much lower concentration, as low as 0.05 $\mu$M per ml. The inhibiting levels of cerous sulfadiazine were found to be similar to those of silver sulfadiazine and zinc sulfadiazine. The results of these tests are summarized in accompanying Table No. 1.

TABLE NO. 1

| Compound Tested | In vitro Inhibition | | | |
| --- | --- | --- | --- | --- |
| | *Pseudomonas aeruginosa* | *Esch. coli* | *Staph. aureus* | *Klebsiella pneumoniae* |
| | *Inhibitory concentrations - $\mu$M per ml | | | |
| Cerous nitrate | 2.5 | 2.5 | 5.0 | 5.0 |
| Silver nitrate | 0.025 | 0.005 | 0.005 | 0.1 |
| Cerous sulfadiazine** | 0.05 | 0.025 | 0.025 | 0.05 |
| Silver sulfadiazine | 0.1 | 0.05 | 0.05 | 0.05 |

*Concentration — $\mu$M/ml which permitted no growth by 48 hours.
Inoculum = 0.2 ml of 1/10,000 dilution of overnight culture.
**Inhibition in vitro with 0.1 $\mu$M/ml of cerous sulfadiazine was reversed when 0.0025 $\mu$M per ml of para-aminobenzoic acid (PABA) was added to the initial reaction mixture. Inhibition with 0.1 $\mu$M silver sulfadiazine is not reversed by PABA. PABA was employed in these tests to measure the role of the sulfadiazine moiety. No such interference was found in trials with burned mice seeded or challenged with *Pseudomonas aeruginosa*.

Further illustrative of the practices of this invention, particularly with respect to the utility of the compounds of this invention, especially cerous sulfadiazine and compositions containing cerous sulfadiazine, in the treatment of burns, mice were scalded to the extent about 30% of the body surface by dipping in water at a temperature of 67° C. for a period of 7 seconds. Subsequent to the scalding operation, 1 hour thereafter, the scalded or burned surfaces were infected or seeded with *Pseudomonas aeruginosa*. After approximately 4 hours the mice were divided at random into three groups and maintained. Some mice, the control mice 40 in number, were not treated with any medication. One group of mice, 40 in number, was treated with a medicament containing about 1% by weight silver sulfadiazine dispersed in a water-dispersible oil-in-water emulsion cream and another group of mice, 40 in number, was treated with a dispersion of cerous sulfadiazine dispersed in a water-dispersible oil-in-water emulsion cream. Fresh medication was applied daily to the scalded surfaces.

In these tests about all the control or untreated mice died 5–7 days after scalding, at which time 15% of those mice treated with silver sulfadiazine had died. Of those mice treated with cerous sulfadiazine only about 10 (25%) died 7 days after scalding. These tests indicate the usefulness of cerous sulfadiazine in the treatment of burns and indicate the superiority of cerous sulfadiazine over silver sulfadiazine. The results of these tests are graphically illustrated in accompanying FIG. I.

Additional tests involving scalded mice were carried out in the manner described hereinabove in connection with the data presented in accompanying FIG. I. In these tests a number of medicaments were employed. These medicaments included an admixture of cerous chloride and cerous nitrate, zinc sulfadiazine, silver sulfadiazine, cerous sulfadiazine, silver sulfadiazine in combination with cerous sulfadiazine and cerous sulfadiazine in combination with zinc sulfadiazine. The zinc sulfadiazine, silver sulfadiazine, cerous sulfadiazine, the combination of silver sulfadiazine and cerous sulfadiazine and the combination of zinc sulfadiazine and cerous sulfadiazine were employed as dispersions at a level 1–2% by weight in a water-dispersible oil-in-water cream emulsion. The results of these tests are graphically illustrated in accompanying FIG. II. As illustrated therein, the combination of zinc sulfadiazine and cerous sulfadiazine was superior to all the other medicaments in these tests. Also in these tests, cerous sulfadiazine was superior to silver sulfadiazine and zinc sulfadiazine and the combination of silver sulfadiazine and cerous sulfadiazine was superior to cerous sulfadiazine alone.

Other tests were carried out demonstrating the effectiveness of cerium sulfadiazine in accordance with this invention in the treatment of burns. In these tests, like the tests reported hereinabove, the results of which are graphically presented in accompanying FIGS. I and II, mice were scalded to the extent of about 30% of body surface by dipping in hot water at a temperature of 67° C. for 7 seconds. Thereupon the scalded or burned surfaces were seeded with a strain of *Pseudomonas aeruginosa* which from previous experience evidenced virulency.

As in the previously described experiments, after seeding the scalded surface with the *Pseudomonas aeruginosa*, the mice were randomly divided into a number of groups. One of these groups (11 mice in number) received no medication and was employed as the control group. The other groups (each 10 in number) received medication. After scalding and challenging with *Pseudomonas aeruginosa* all the mice were maintained and for those groups receiving medication the medication was applied daily to the burned surface. One group received as the medication 1% by weight silver sulfadiazine dispersed in a water-dispersible oil-in-water emulsion. Another group received as medication silver butyrate dispersed in a water-dispersible oil-in-water emulsion carrier at a concentration of 30mM per kilogram. Another group received cerium sulfadiazine (cerous sulfadiazine) prepared from cerous chloride and sodium sulfadiazine dispersed in a waterdispersible oil-in-water emulsion carrier at a concentration of 30mM/kg. Still another group of mice, 10 in number, received as medication the cerium sulfadiazine (cerous sulfadiazine) dispersed in a water-dispersible oil-in-water emulsion carrier at a cerous sulfadiazine concentration of 30mM/kg.

Another group, 10 in number, received as medication cerium sulfadiazine (cerous sulfadiazine) and para-aminobenzoic acid dispersed in an oil-in-water emulsion carrier at a concentration of 30mM/kg cerous sulfadiazine and 3mM/kg of para-aminobenzoic acid. Still another group (10 in number) received as medication cerium sulfadiazine (cerous sulfadiazine) and zinc sulfadiazine dispersed in an oil-in-water emulsion carrier at a concentration of 15mM/kg cerous sulfadiazine and 15mM/kg zinc sulfadiazine. Also, another group of mice (10 in number) received as medication cerium sulfadiazine (cerous sulfadiazine), zinc sulfadiazine and silver sulfadiazine dispersed in a water-dispersible oil-in-water emulsion at a concentration of 10mM/kg cerous sulfadiazine, 10mM/kg zinc sulfadiazine and 10mM/kg silver sulfadiazine. The results of these tests are graphically set forth in accompanying FIG. III. It had already been indicated that inorganic cerium salts by themselves were not effective.

Of particular interest is the fact that the combination of cerous sulfadiazine and para-aminobenzoic acid afforded best protection. The results with respect to the combination of cerous sulfadiazine and para-aminobenzoic acid, a well recognized inhibitor of sulfonamides, were surprising since in vitro studies showed that para-aminobenzoic acid inhibited in part both cerous sulfadiazine and zinc sulfadiazine but did not inhibit silver sulfadiazine.

In the results reported herein, see FIG. III, the medicament or the active component(s) in the medicament was employed at a concentration level of 30mM/kg.

In the practices of this invention cerium sulfadiazine, e.g. cerous sulfadiazine, or cerium sulfadiazine-containing compositions which might contain other active medicaments, is applied in an effective antibacterial amount to burned surfaces. When cerium sulfadiazine, e.g. cerous sulfadiazine, is employed in combination with another medicament, the amount of applied cerium sulfadiazine might be reduced proportionately to the amount of the other medicament, e.g. silver sulfadiazine and/or zinc sulfadiazine along with the cerium sulfadiazine. As the test results illustrated in FIG. III show, the protection afforded by cerium sulfadiazine is enhanced when a minor amount, about 10 mol % relative to the cerium sulfadiazine, of para-aminobenzoic acid is added to the cerium sulfadiazine.

In burn treatment employing cerium sulfadiazine, e.g. cerous sulfadiazine, or cerium sulfadiazine-containing compositions, all in accordance with the practices of this invention, the cerium sulfadiazine and/or cerium sulfadiazine-containing compositions can be added directly to the burn or wound surface, such as by the direct application of cerous sulfadiazine or cerous sulfadiazine-containing compositions in powder form or admixed or encapsulated with a suitable physiologically acceptable carrier or encapsulating agent or incorporated in a bandage or a film-form carrier. Desirably, in the practice of this invention, the cerous sulfadiazine or cerous sulfadiazine-containing composition is applied to the surface dispersed in a petrolatum or cream-like carrier, preferably dispersed in a water-dispersible or water-soluble oil-in-water emulsion.

When cerium sulfadiazine-containing compositions of this invention are employed, as indicated hereinbefore, the cerium sulfadiazine component thereof is present in an effective antibacterial amount or concentration. Suitable such compositions would contain the cerium sulfadiazine component in an amount in the range from about 0.1 to about 10.0% by weight, more or less, preferably in the range from about 0.5 to about 2.5% by weight. Other active medicaments, such as para-aminobenzoic acid, zinc sulfadiazine and/or silver sulfadiazine, are usefully incorporated along with the cerium sulfadiazine, in which instance such other medicaments may be present in an amount from about 0.01 up to about 1 to 5% by weight of the composition.

In the practices of this invention wherein cerium sulfadiazine, e.g. cerous sulfadiazine, is applied to the burn surface, particularly in the instance wherein the cerium sulfadiazine is employed with another component as a medicament, such as zinc sulfadiazine, silver sulfadiazine and/or para-aminobenzoic acid, these other components may be added along with or separately, either before or after, with respect to the application of cerium sulfadiazine to the burn wound or surface.

It is preferred in the practice of this invention to apply the cerium sulfadiazine to the burn surface by way of a composition wherein the cerium sulfadiazine is dispersed in a water-soluble or water-dispersible hydrophilic cream, such as an oil-in-water carrier or cream.

Compositions in accordance with this invention containing cerium sulfadiazine, e.g. cerous sulfadiazine, dispersed in a water-dispersible hydrophilic carrier or ointment, e.g. hydrophilic oil-in-water emulsion, may be characterized by the following components and percentages by weight as set forth in accompanying Table No. 2.

Table No. 2

| Component | % By Weight |
|---|---|
| Petrolatum | 0–25 |
| Water-insoluble $C_{16}$–$C_{22}$ fatty alcohol | 7–45 |
| Emollient | 0–15 |
| Emulsifying Agents, preferably non-ionic | 4–16 |
| Humectant | 7–40 |
| Cerium Sulfadiazine (e.g. cerous sulfadiazine) | 0.1–10 |
| Preservative | 0–0.3 |
| Deionized or Distilled Water q.s. | 100 |
| Other Medicaments* | 0.01–5 |

*Zinc sulfadiazine, silver sulfadiazine and/or para-aminobenzoic acid.

The fatty alcohols, stearyl alcohol, cetyl alcohol, lauryl alcohol and myristyl alcohol are useful in the preparation of compositions in accordance with this invention. These preferential oil-soluble fatty alcohols act as a stiffener in the resulting composition. As the emollient, isopropyl myristate, lanolin, lanolin derivatives, isopropyl palmitate, isopropyl stearate and the corresponding sebacates and other known emollients are suitable. As the emulsifying agent sorbitan monooleate, such an amount in the range 0.5–4 percent by weight, and polyoxyl 40 stearate in an amount in the range 7–12 percent by weight, both non-ionic emulsifying agents are satisfactory. A suitable humectant would be propylene glycol, sorbitol or glycerin and mixtures thereof, all being watersoluble compounds. A suitable preservative would be any of the useful conventional water-soluble preservatives which exhibit antimicrobial activity, such as sorbic acid, benzoic methylparaben and propylparaben and mixtures thereof.

In the formulation of a cerium sulfadiazine-containing composition having the composition set forth in Table No. 2 hereinabove, as the amount of aqueous phase is increased, the solid content, i.e. the water-immiscible or water-insoluble components, e.g. fatty alcohol, such as stearyl alcohol, and/or petrolatum, must also be increased relatively to help stiffen the composition. The preservative, e.g. methylparaben, is employed in the formulation only as a preservative for the overall composition and, as indicated, methylparaben was found to be a satisfactory preservative. Methylparaben, as indicated, however, may also be used in combination with propylparaben.

Accordingly, compositions useful in the practices of this invention would include compositions comprising 0–25 percent by weight petrolatum, 7–45 percent by weight stearyl alcohol, 0–15 percent by weight isopropyl myristate, 5–20 percent by weight of an emulsifying agent, 7–40 percent by weight propylene glycol, 0.5–10 percent by weight cerium sulfadiazine (cerous sulfadiazine) and about 0.01–5.0 percent other medicaments, if desired, in the resulting composition, the remainder being water, as required to bring the total percentages to 100 percent. Other compositions useful would include compositions consisting essentially of 0.5–2 percent by weight cerium sulfadiazine (cerous sulfadiazine), 7–8 percent by weight propylene glycol, 38–44 percent by weight water, 14–18 percent by weight petrolatum, 14–18 percent by weight stearyl alcohol, 5–8 percent by weight isopropyl myristate, 0.5–2 percent by weight sorbitan monooleate and 6–10 percent by weight polyoxyl 40 stearate and 0.05–2 percent by weight other medicaments, if desired. Another composition useful in the practice of this invention would include the composition consisting essentially of 0–25 percent by weight petrolatum, 7–45 percent by weight of an aliphatic fatty alcohol having a carbon atom content in the range $C_{16}$–$C_{22}$, 0–15 percent by weight of an emollient, 7–16 percent by weight of an emulsifying agent, 7–14 percent by weight of a humectant, 0.2–5.0 percent by weight cerous sulfadiazine and 0.1–2 percent by weight other medicaments, e.g. zinc sulfadiazine, silver sulfadiazine and/or para-aminobenzoic acid.

Various hydrophilic or oil-in-water emulsion bases are commercially available and are suitable in the preparation of compositions in accordance with this invention, e.g. Neobase manufactured by Burroughs-Wellcome, Unibase manufactured by Parke-Davis, Emulsion Base manufactured by Almay, Dermabase manufactured by Marcelle, Cetaphil manufactured by Texas Pharmacal. In general, hydrophilic bases, such as hydrophilic bases of the oil-in-water emulsion type, are characterized by the ease with which they may be removed from the skin by washing with water.

By way of summarizing or indicating the efficacy of cerium sulfadiazine, e.g. cerous sulfadiazine, in the treatment of burns, in Table No. 3 there are set forth the results of a total of 11 separate animal (mice) experiments of the type described hereinabove wherein various medicaments, including cerous sulfadiazine, were employed. The results set forth in accompanying Table No. 3 show that cerous sulfadiazine when employed as a medicament in 100 burned mice was effective such that only 5 percent of the burned mice treated with cerous sulfadiazine died during the 5–7 day period post-burn as compared with 100% of the untreated mice.

Table No. 3

| Medicament | No. of Mice | Mortality* |
|---|---|---|
| Controls (untreated) | 110 | 100% (5–7 days) post-burn |
| Silver sulfadiazine | 110 | 15% |
| Cerous sulfadiazine | 100 | 5% |
| Zinc sulfadiazine | 50 | 20% |
| Silver sulfadiazine + | | |

Table No. 3-continued

| Medicament | No. of Mice | Mortality* |
|---|---|---|
| cerous sulfadiazine | 40 | 10% |
| Zinc sulfadiazine + cerous sulfadiazine | 40 | 3% |
| Silver sulfadiazine + zinc sulfadiazine + cerous sulfadiazine | 30 | 10% |
| Water-soluble inorganic cerous salt (Ce$^{+++}$) | 30 | 67% |

*Mortality at day or day after 100% mortality in untreated mice in each experiment (positive blood culture). In treated mice, often after 6–9 days death occur without positive blood cultures, i.e. death due to causes other than infection, e.g. urinary obstruction due to burn of genitalia, etc.

Clinical trials employing cerium sulfadiazine (cerous sulfadiazine) were carried out. In these trials, cerous sulfadiazine in admixture with silver sulfadiazine in a water-dispersible oil-in-water emulsion carrier were employed. The amount of silver sulfadiazine in the carrier was about 1% by weight and the amount of cerous sulfadiazine varied in the range 1–4% by weight. In these tests grossly infected burn wounds on both legs or arms were treated for 5–6 days. The medicament containing cerous sulfadiazine and silver sulfadiazine was applied to one grossly infected arm or leg and the medicament containing only silver sulfadiazine was similarly applied to the other grossly infected arm or leg. The arm or leg treated with the admixture of silver sulfadiazine and cerous sulfadiazine showed a more rapid reduction in the amount of infection than the other arm or leg similarly treated with the medicament containing only silver sulfadiazine. No pain, no evidence of irritation and no toxicity were observed in these clinical trials.

Cerous sulfadiazine compositions in accordance with this invention, e.g. cerous sulfadiazine in combination with silver sulfadiazine, were also applied to infected wounds (not burns). The application of the combination of cerous sulfadiazine and silver sulfadiazine to such wounds also appeared to be effective and the combination of medicaments appeared to be well tolerated, e.g. no pain.

FIG. IV of the drawings further graphically illustrates the advantages of the practices of this invention. The data presented in FIG. IV are based on tests wherein mice were scalded, about 30% of the body, in the manner reported hereinabove with respect to FIGS. I, II and III. Some of the scalded mice, the control group, were untreated. The remaining scalded mice, after having been randomly segregated into groups like the control group, were treated with various medicaments, namely, silver sulfadiazine, cerous sulfadiazine and para-aminobenzoic acid, silver sulfadiazine and cerous sulfadiazine, zinc sulfadiazine and cerous sulfadiazine, zinc sulfadiazine and silver sulfadiazine and cerous sulfadiazine, and cerous sulfadiazine. These medicaments were applied daily to the scalded or burned surfaces of the mice in a suitable carrier, such as a water-dispersible oil-in-water emulsion carrier as described hereinabove, see particularly the tests and data reported in connection with FIG. III.

In the results of the tests graphically reported or illustrated in FIG. IV, the data considered most important are the percent mortality of the treated mice when the mortality of the control or untreated mice reached 100%. As indicated hereinbefore, it is usual for all the mice, including the treated mice, to die eventually since the burn injuries are invariably fatal even when mice are not challenged with an infectious microorganism, such as *Pseudomonas aeruginosa*.

In the tests reported in FIG. IV, it is shown that the mortality of the control group was 100% 8 days after scalding and infection with *Pseudomonas aeruginosa*. On the other hand, the cerous sulfadiazine treated mice showed substantially no mortality. Although the cerous sulfadiazine and para-aminobenzoic acid treated mice showed about 60% mortality, the combination of medicaments of zinc sulfadiazine, silver sulfadiazine and cerous sulfadiazine, silver sulfadiazine and cerous sulfadiazine, and zinc sulfadiazine and cerous sulfadiazine all also showed outstanding effectiveness. The mice treated with these combinations of medicaments only showed 20% mortality 8 days post-scald and infection as compared with 100% mortality of the control or untreated mice. The data presented in FIG. IV show the effectiveness of cerous sulfadiazine, alone or in combination, as a medicament in the treatment of burns.

In the disclosures of this invention, it is broadly indicated that cerium sulfadiazine is effective in burn therapy. Also, in the disclosures of this invention emphasis has been placed on the effectiveness of cerous sulfadiazine in burn therapy. The cerium sulfadiazine or cerous sulfadiazine need not be the full sulfadiazine salt, i.e. all the valences available from the cerium moiety (ceric or cerous) need not be occupied or utilized by the sulfadiazine moiety. For example, partial salts of cerium sulfadiazine or cerous sulfadiazine are useful, e.g. cerous sulfadiazine chloride, such as may be indicated by the formula Ce(SD)$_n$(Cl)$_m$ wherein $n$ may be 1 or 2 and wherein when $n$ is 1 $m$ is 2 and when $n$ is 2 $m$ is 1. The essential features of this invention appear to be attributable to the combination of cerium, e.g. cerous ion, in combination with the sulfadiazine moiety. Other physiologically acceptable anions in addition to sulfadiazine, such as may be present in a partial cerium sulfadiazine or cerous sulfadiazine salt, might also be present, e.g. chloride ion.

Additionally, other so-called rare earth sulfadiazine compounds and other rare earth sulfadiazine-containing compositions would also appear to be useful in the practices of this invention. Other suitable rare earth sulfadiazines in addition to cerium sulfadiazines, including cerous sulfadiazine, preferably the lower valence states thereof, are the thorium sulfadiazines, the lanthanum sulfadiazines, the samarium sulfadiazines, the praseodymium sulfadiazines and the other rare earth sulfadiazines. Elements which have also been identified as rare earth elements or metals are Sc, Y, Nd, Pm, Eu, Gd, Tb, Dy, Ho, Er, Yb and Lu.

As will be apparent to those skilled in the art in the light of the foregoing disclosures, many modifications, alterations and substitutions are possible in the practice of this invention without departing from the spirit or scope thereof.

I claim:

1. A composition useful in treating burns consisting essentially of an effective antibacterial amount of cerous sulfadiazine and a water-dispersible, hydrophilic carrier therefor, wherein said cerous sulfadiazine is dispersed in said carrier.

2. A composition useful in treating burns consisting essentially of an effective antibacterial amount of cerous sulfadiazine and a semi-soft or cream-like, water-dispersible or water-soluble oil-in-water emulsion carrier wherein said cerous sulfadiazine is dispersed in said carrier.

3. A composition in accordance with claim 2 wherein from about 0.1 to about 10% by weight of cerous sulfadiazine is dispersed in said carrier.

4. A composition useful in treating burns comprising an effective antibacterial amount of an admixture of cerous sulfadiazine and para-amino benzoic acid.

5. A composition useful in treating burns comprising an effective antibacterial amount of an admixture of cerous sulfadiazine and zinc sulfadiazine.

6. A composition useful in treating burns comprising an effective antibacterial amount of an admixture of cerous sulfadiazine and silver sulfadiazine.

7. A composition useful in treating burns comprising an effective antibacterial amount of an admixture of cerous sulfadiazine, silver sulfadiazine and zinc sulfadiazine.

8. A composition useful in treating burns comprising an effective antibacterial amount of an admixture of cerous sulfadiazine, silver sulfadiazine, zinc sulfadiazine and para-amino benzoic acid.

9. A composition in accordance with claim 4 consisting essentially of cerous sulfadiazine wherein said cerous sulfadiazine is present in an amount in the range 0.1–10.0% by weight of said composition and wherein said para-aminobenzoic acid is present in an amount in the range 0.1–5% by weight.

10. A composition in accordance with claim 5 consisting essentially of cerous sulfadiazine and zinc sulfadiazine wherein said cerous sulfadiazine is present in an amount in the range 0.1–10.0% by weight and wherein said zinc sulfadiazine is present in an amount in the range 0.1–5% by weight.

11. A composition in accordance with claim 6 consisting essentially of cerous sulfadiazine and silver sulfadiazine wherein said cerous sulfadiazine is present in an amount in the range 0.1–10.0% by weight and wherein said silver sulfadiazine is present in an amount in the range 0.1–5% by weight.

12. A composition in accordance with claim 7 consisting essentially of cerous sulfadiazine, silver sulfadiazine and zinc sulfadiazine wherein said cerous sulfadiazine is present in an amount in the range 0.1–10.0% by weight, said silver sulfadiazine is present in an amount in the range 0.1–5% by weight and said zinc sulfadiazine is present in an amount in the range 0.1–5% by weight.

13. A composition in accordance with claim 8 wherein said cerous sulfadiazine is present in an amount in the range 0.1–10.0% by weight, said silver sulfadiazine is present in an amount in the range 0.1–5% by weight, said zinc sulfadiazine is present in an amount in the range 0.1–5% by weight and said para-aminobenzoic acid is present in an amount in the range 0.1–5% by weight.

14. A method of treating burns in man and animal which comprises topically applying to the affected surface an effective antibacterial amount of a composition in accordance with claim 5.

15. A method of treating burns in man and animal which comprises topically applying to the affected surface an effective antibacterial amount of a composition in accordance with claim 5.

16. A method of treating burns in man and animal which comprises topically applying to the affected surface an effective antibacterial amount of a composition in accordance with claim 8.

17. A method of treating burns in man and animal which comprises topically applying to the affected surface an effective antibacterial amount of cerous sulfadiazine.

18. A method of treating burns in man and animal which comprises topically applying to the affected surface an effective antibacterial amount of cerous sulfadiazine, said cerous sulfadiazine being dispersed in a water-dispersible, hydrophilic carrier.

19. A method in accordance with claim 18 wherein said carrier is a semi-soft or creamlike, water-dispersible or water-soluble oil-in-water emulsion.

* * * * *

UNITED STATES PATENT AND TRADEMARK OFFICE
CERTIFICATE OF CORRECTION

PATENT NO. : 4,078,058
DATED : March 7, 1978
INVENTOR(S) : Charles L. Fox, Jr.

It is certified that error appears in the above-identified patent and that said Letters Patent are hereby corrected as shown below:

Column 2, under Table No. 1, "in vitro" should be underscored

Column 3, line 63, "waterdispersible" should be hyphenated

Column 4, line 25, "in vitro" should be underscored

Column 5, line 57 "watersoluble" should be hyphenated

Column 7, under Table No. 3-continued, "death" should read -- deaths --

Column 10, (Claim 15, line 4) "claim 5" should read -- claim 6 --

Signed and Sealed this

Eleventh Day of September 1979

[SEAL]

Attest:

Attesting Officer

LUTRELLE F. PARKER
Acting Commissioner of Patents and Trademarks